US008137668B2

(12) United States Patent
Li

(10) Patent No.: US 8,137,668 B2
(45) Date of Patent: *Mar. 20, 2012

(54) METHODS AND COMPOSITIONS FOR GENERATING HUMAN MONOCLONAL ANTIBODIES

(75) Inventor: Ronghao Li, Millbrae, CA (US)

(73) Assignee: MacroGenics, Inc., Rockville, MD (US)

(*) Notice: Subject to any disclaimer, the term of this patent is extended or adjusted under 35 U.S.C. 154(b) by 422 days.

This patent is subject to a terminal disclaimer.

(21) Appl. No.: 11/482,660

(22) Filed: Jul. 6, 2006

(65) Prior Publication Data

US 2006/0252124 A1 Nov. 9, 2006

Related U.S. Application Data

(60) Continuation of application No. 10/327,423, filed on Dec. 20, 2002, now abandoned, which is a division of application No. 09/491,894, filed on Jan. 26, 2000, now Pat. No. 6,541,225.

(51) Int. Cl.
*C07K 16/24* (2006.01)
*C12N 5/07* (2010.01)
*C12P 21/08* (2006.01)

(52) U.S. Cl. .................. 424/133.1; 435/326; 530/388.23

(58) Field of Classification Search ............... 424/133.1; 435/326; 530/388.23
See application file for complete search history.

(56) References Cited

U.S. PATENT DOCUMENTS

| | | | |
|---|---|---|---|
| 4,643,971 A | 2/1987 | Fradet et al. |
| 4,683,195 A | 7/1987 | Mullis et al. |
| 4,683,202 A | 7/1987 | Mullis |
| 5,326,696 A | 7/1994 | Chang |
| 5,747,034 A | 5/1998 | de Boer et al. |
| 5,814,318 A | 9/1998 | Lonberg et al. |
| 5,882,644 A | 3/1999 | Chang et al. |
| 5,939,598 A | 8/1999 | Kucherlapati et al. |
| 6,004,528 A | 12/1999 | Bergstein |
| 6,150,584 A | 11/2000 | Kucherlapati et al. |
| 6,541,225 B1 | 4/2003 | Li |
| 2003/0109006 A1 | 6/2003 | Li |

FOREIGN PATENT DOCUMENTS

| | | |
|---|---|---|
| EP | 0 218 158 A2 | 4/1987 |
| EP | 0 488 470 A1 | 6/1992 |
| EP | 0 856 520 A1 | 8/1998 |
| WO | WO-94/11509 A2 | 5/1994 |
| WO | WO-94/11509 A3 | 5/1994 |
| WO | WO-95/22619 A1 | 8/1995 |
| WO | WO-97/23613 A2 | 7/1997 |
| WO | WO-97/23613 A3 | 7/1997 |
| WO | WO-98/52976 A1 | 11/1998 |
| WO | WO-01/55216 A1 | 8/2001 |

OTHER PUBLICATIONS

Habersetzer, F. et al. (Sep. 15, 1998). "Characterization of Human Monoclonal Antibodies Specific to the Hepatitis C Virus Glycoprotein E2 with in Vitro Binding Neutralization Properties," *Virology* 249(1):32-41.

Shinmoto, H. (May 1999). "Preparation of Human Antibody-Secreting Cells for Food Allergens. Application to the Elucidation of Human Monoclonal Antibody Food Allergies has Begun," *Chemistry and Biology* 37(5):286-287, with certified English Translation, 6 pages.

Ausubel, F.M. et al., eds. (1987). *Current Protocols in Molecular Biology*. John Wiley & Sons, Inc., pp. iii-xii, (Table of Contents Only.).

Barnes, D. et al. (1980). "Methods for Growth of Cultured Cells in Serum-Free Medium," *Anal. Biochem.* 102:255-270.

Bird, R.E. et al. (1988). "Single-Chain Antigen-Binding Proteins," *Science* 242:423-426.

Callard, R. et al., eds. (1994). *The Cytokine FactsBook*. Academic Press: San Diego, CA., pp. v., (Table of Contents Only.).

Carroll, K. et al. (1990). "Parameters Involved in the In Vitro Immunization of Tonsilar Lymphocytes: Effects of rIL-2 and Muramyl Dipeptide," *Hybridoma* 9(1):81-89.

Chatal, J.F. et al. (1985). "Clinical Prospective Study with Radioiodinated Monoclonal Antibodies Directed Against Colorectal Cancer" Chapter 8 *In Monoclonal Antibodies for Cancer Detection and Therapy*. Baldwin, R.W. et al., eds., Academic Press: London, pp. 159-180.

Crossland, K.D. et al. (1991). "T Cells from Tumor-Immune Mice Nonspecifically Expanded in vitro with Anti-CD3 Plus IL-2 Retain Specific Function in vitro and can Eradicate Disseminated Leukemia in vivo," *J. Immunol.* 146(12):4414-4420.

DeMaeyer, E. et al., eds. (1988). *Interferons and Other Regulatory Cytokines*. John Wiley & Sons: New York, pp. ix-x, (Table of Contents Only.).

Freshney, R.I., ed. (1987). *Animal Cell Culture: A Practical Approach*. IRL Press: Oxford, pp. vii-xii, (Table of Contents Only.).

Greenman, J. et al. (1991). "Characterization of a New Monoclonal Anti-Fcγ RII Antibody, AT10, and its Incorporation into a Bispecific F(ab')$_2$ Derivative for Recruitment of Cytotoxic Effectors," *Mol. Immunol.* 28(11):1243-1254.

Harlow, E. et al., eds. (1988). *Antibodies: A Laboratory Manual*, Cold Spring Harbor Laboratory Press: New York, pp. iii-ix, (Table of Contents Only.).

Huston, J.S. et al. (1988). "Protein Engineering of Antibody Binding Sites: Recovery of Specific Activity in an Anti-Digoxin Single-Chain Fv Analogue Produced in *Escherichia coli*," *Proc. Natl. Acad. Sci.* 85:5879-5883.

Jakoby, W.B. et al., eds. (1979). *Methods in Enzymology*, vol. LVIII, Cell Culture, Academic Press: New York, pp. v-viii (Table of Contents Only.).

(Continued)

*Primary Examiner* — Lynn Bristol
(74) *Attorney, Agent, or Firm* — William C. Schrot; Jeffrey I. Auerbach; The Auerbach Law Firm, LLC

(57) ABSTRACT

The present invention provides a method for generating human monoclonal antibodies, especially those that are specific for surface antigens representative of a particular cell type. The present invention also includes populations of monoclonal antibodies produced by the invention methods, populations of polynucleotides comprising sequences encoding the immunoglobulins or fragments thereof, which are capable of binding to antigens representative of a cell type of interest.

8 Claims, 3 Drawing Sheets

OTHER PUBLICATIONS

Jansen, F.K. et al. (1985). "Efficiency and Tolerance of the Treatment with Immuno-A-Chain-Toxins in Human Bone Marrow Transplantations" Chapter 11 *In Monoclonal Antibodies for Cancer Detection and Therapy*. Baldwin, R.W. et al., eds., Academic Press: London, pp. 223-267.

Koda, K. et al. (1990). "In Vitro Immunization for the Production of Human Monoclonal Antibody," *Human Antibod. Hybridomas.* 1(1):15-22.

Kwekkeboom, J. et al. (Mar. 15, 1993). "An Efficient Procedure for the Generation of Human Monoclonal Antibodies Based on Activation of Human B Lymphocytes by a Murine Thymoma Cell Line," *J. Immunol. Methods.* 160(1):117-127.

Mather, J.P. et al., eds. (1998). *Introduction to Cell and Tissue Culture*. Plenum Press: New York, pp. xi-xv, (Table of Contents Only.).

McPherson, M.J. et al., eds. (1995). *PCR 2: A Practical Approach*. IRL Press: Oxford, pp. ix-xvii, (Table of Contents Only.).

Mullis, K.B. et al. (1987). "Specific Synthesis of DNA in Vitro via a Polymerase-Catalyzed Chain Reaction" Chapter 21 *In Methods in Enzymology*. Academic Press, 155:335-351.

Olsnes, S. et al. (1982). "Chimeric Toxins," *Pharmac. Ther.* 15:355-381.

Sambrook, J. et al., eds. (1989). *Molecular Cloning: A Laboratory Manual: Second Edition*. Cold Spring Harbor Laboratory Press, pp. xi-xxxviii, (Table of Contents Only.).

Sato, G.H. et al., eds. (1982). *Growth of Cells in Hormonally Defined Media:Book A*. Cold Spring Harbor Laboratory Press, pp. xi-xix, (Table of Contents Only.).

Sato, G.H. et al., eds. (1982). *Growth of Cells in Hormonally Defined Media:Book B*. Cold Spring Harbor Laboratory Press, pp. v-xiii, (Table of Contents Only.).

Sidorova, E. et al. (1997). "Human Monoclonal Antibodies to Viral Peptides," *Human Antibodies* 8(2):65-69.

Steenbakkers, P.G.A. et al. (Oct. 1993). "Efficient Generation of Human Anti-Cytomegalovirus IgG Monoclonal Antibodies from Preselected Antigen-Specific B Cells," *Human Antibodies and Hybridomas* 4:166-173.

Thorpe, P.E. et al. (1982). "Monoclonal Antibody-Toxin Conjugates: Aiming the Magic Bullet" Chapter 7 *In Monoclonal Antibodies in Clinical Medicine*. McMichael, A.J. et al., eds., Academic Press:London, pp. 168-201.

Vitetta, E.S. et al. (1987). "Redesigning Nature's Poisons to Create Anti-Tumor Reagents," *Science* 238:1098-1104.

Ward, E.S. et al. (1989). "Binding Activities of a Repertoire of Single Immunoglobulin Variable Domains Secreted from *Escherichia coli*," *Nature* 341:544-546.

Weaver, C.H. et al. (1993). "Syngeneic Transplation with Peripheral Blood Mononuclear Cells Collected after the Administration of Recombinant Human Granulocyte Colony-Stimulating Factor," *Blood* 82(7):1981-1984.

Winter, G. et al. (1991). "Man-Made Antibodies," *Nature* 349:293-299.

Flow Chart for Producing Human Monoclonal Antibodies against Cell Surface Antigens

METHODS AND COMPOSITIONS FOR GENERATING HUMAN MONOCLONAL ANTIBODIES

CROSS REFERENCE TO RELATED APPLICATIONS

This application is a continuation of U.S. application Ser. No. 10/327,423, filed Dec. 20, 2002, which is a divisional of U.S. application Ser. No. 09/491,894, filed Jan. 26, 2000, now U.S. Pat. No. 6,541,225, all of which are incorporated herein by reference in their entirety.

TECHNICAL FIELD

This invention is in the field of immunology. Specifically, the invention relates to the generation of human monoclonal antibodies, especially those that are specific for surface antigens representative of a particular cell type. The compositions and methods embodied in the present invention are particularly useful for generating human monoclonal antibodies that are of major diagnostic and/or therapeutic potential.

BACKGROUND OF THE INVENTION

The discovery by Kohler and Milstein of murine hybridomas capable of secreting specific monoclonal antibodies against predetermined antigens ushered a new era in the field of clinical immunology. The clonal selection and immortality of such hybridoma cell lines assure the monoclonality, monospecificity and permanent availability of their antibodies. However, murine antibodies have severe limitations in clinical applications for humans because of their intrinsic immunogenicity which often leads to undesirable immune responses. For instance, when immunocompetent human patients are administered therapeutic doses of mouse monoclonal antibodies, the patients produce antibodies against the mouse immunoglobulin molecules; these human anti-mouse antibodies neutralize the therapeutic antibodies and can cause acute toxicity. Hence, it would be desirable to generate antibodies that have no such drawbacks.

Generation of human monoclonal antibodies has been practically difficult for a number of reasons. First, it is not practical to immunize a human being with an immunogen of interest. The human antibodies which have been produced have been based on the adventitious presence of an available spleen. While four alternative ways of generating human monoclonal antibodies with desired antigen-binding specificity have been developed, they also have pronounced disadvantages. The first approach involves the use of recombinant DNA technology to generate a chimeric antibody. Such antibody is produced by fusing the constant regions of the heavy and light chains of a human immunoglobulin with the variable regions of the non-human antibody that confirm the antigen-binding specificity. While the resulting chimeric partly xenogeneic antibody is substantially more useful than using a fully xenogeneic antibody, it still has a number of disadvantages. The identification, isolation and joining of the variable and constant regions require substantial work. In addition, the joining of a constant region from one species to a variable region from another species may change the specificity and affinity of the variable regions, so as to lose the desired properties of the variable region. Furthermore, there are framework and hypervariable sequences specific for a species in the variable region. These framework and hypervariable sequences may result in undesirable antigenic responses. A variation of this approach is to replace residues outside the antigen-binding domains of a non-human antibody with the corresponding human sequences (WO 94/11509). Such a process is again labor intensive.

The second approach for production of human monoclonal antibodies is the use of xenogenic mice as described in U.S. Pat. No. 5,814,318 and U.S. Pat. No. 5,939,598. These genetically engineered mice are capable of expressing certain unrearranged human heavy and light chain immunoglobulin genes, with their endogenous immunoglobulin genes being inactivated. Although the "xenomouse" represents an alternative system for generating human antibodies, it does not necessarily fully mimic the human immune system: first, the entire repertoire of immunoglobulins has not been duplicated in the mice; second, the incomplete inactivation of endogenous immunoglobulin genes may result in chimeric antibodies; third, the identification of the desired monoclonal antibodies generally involves conventional hybridoma techniques, which in turn requires extensive screening and subcloning a large number of hybridomas in order to identify the desired antibodies.

The third approach of producing human monoclonal antibodies is phage display library construction. The process proceeds with extraction of mRNA from a repertoire of human peripheral blood cells, followed by construction of a cDNA library comprising sequences of the variable regions of preferably all immunoglobulins. The cDNAs are then inserted into phages to which to display the immunoglobulin variable region as Fab fragments. Theoretically, if the phage library is large enough, it is possible to isolate the particular phage displaying the desired Fab fragment by panning the phages against the antigen of interest. However, this method is generally applicable only to substantially purified antigens, and not to a mixture of antigens such as thousands of those surface antigens expressed on the cell.

Finally, immortalized human B cells have been employed for monoclonal antibody production. This approach involve the steps of: (a) isolation of peripheral blood lymphocytes enriched in B cells; (b) transformation of the B cells with EBV-viruses or fusion with immortalized human lymphoblastoid cells, followed by massive screening for the B cell transformants or hybridomas exhibiting the desired antigen-binding specificity. B cell transformation itself is an inefficient process yielding at best 0.1-10% stable transformants, thus most B cells with the desired specificity are lost in the pool used for subsequent selection process. Whereas researchers (e,g, Abe, Tsutomu et al. in EP 0218158) have attempted to enrich the population of B cells expressing the desired immunoglobulin by in vitro immunization/activation with the antigen of interest; the activation is again inefficient in the sense that non-specific B cells also proliferate during this process. The identification of specific B cells thus largely depends on the final stage of screening, during which tens and thousands of transformed B cell clones are tested for their abilities to bind the antigen. Like the aforementioned methods, this approach is time consuming, labor intensive, and not amenable to high throughput antibody screening and production.

Thus, there remains a considerable need for alternative routes for generating human monoclonal antibodies.

SUMMARY OF THE INVENTION

A principal aspect of the present invention is the design of an efficient screening technique applicable for the generation of human monoclonal antibodies. This technique allows production of specific antibodies with minimal labor. It is particularly useful for large-scale production of populations of human monoclonal antibodies that are immunoreactive with antigens representative of a particular cell type. Distinguished from the above-mentioned approaches that involve generation of hybridomas and/or immortalized B cells, the methods of this invention employ non-transformed B cells, and generate expanded non-transformed B cell clones with required antigen-binding specificity for antibody production and/or isolation of the genes encoding the antibody.

Specifically, the present invention provides a method for generating human monoclonal antibodies immunoreactive with a desired antigen, the method comprising: (a) providing an isolated population of human lymphocytes comprising a plurality of non-transformed human B lymphocytes; (b) selecting the non-transformed human B lymphocytes that specifically bind to the desired antigen; (c) culturing the B lymphocytes of (b) under conditions favorable for B cell proliferation to yield a plurality of isolated non-transformed B cell clones producing the human monoclonal antibodies immunoreactive with the desired antigen, and d) optionally isolating the non-transformed B cell clones.

In one aspect, selecting the non-transformed human B lymphocytes comprises contacting the population of human lymphocytes with the desired antigen under conditions favorable for specific binding of B lymphocytes to the desired antigen, and separating unbound B lymphocytes from B lymphocytes bound to the desired antigen.

In another aspect, the method outlined above further comprises: (e) isolating a polynucleotide comprising sequences encoding an antigen-binding fragment of the heavy chain of the human monoclonal antibody from the isolated non-transformed B cell clone of (d); (f) isolating a polynucleotide comprising sequences encoding an antigen-binding fragment of the light chain of the human monoclonal antibody from the isolated non-transformed B cell clone of (d); and (g) expressing the polynucleotides of (e) and (f) to yield the human monoclonal antibody or an antigen binding fragment thereof.

The isolation of the polynucleotide encoding the heavy chain may precede, or carry out subsequent to, or concurrently with the isolation of the polynucleotide encoding the light chain.

In a separate aspect, the antigen binding fragment encoded by the polynucleotides of the invention may be selected from the group consisting of bispecific antibodies, chimeric antibodies, Fab, F(ab')2, single chain V region fragments (scFv) and fusion polypeptides, wherein the fusion polypeptide comprises the antigen binding fragment conjugated to a chemically functional moiety. Within this embodiment, the term "moiety" encompasses signal peptides, agents that enhance immunologic reactivity, agents that facilitate coupling to a solid support, vaccine carriers, bioresponse modifiers, toxins, detectable labels, and drugs.

In yet another separate aspect, the antigen employed in the antibody generation process is a biological or chemical compound. The antigen may be a cellular protein, such as a receptor ligand, secreted protein, cell surface receptor, cytosolic protein, and nuclear protein. In a preferred embodiment, the antigen is a surface antigen presented by an intact cell. Where an intact cell is employed for antigen presentation, the cell is preferably a eukaryotic cell, whose surface is free of serum.

In still yet another aspect, the polynucleotides encoding the immunoglobulins or fragments thereof are expressed by one or more gene delivery vehicle in a host cell. Suitable gene delivery vehicles include viral vectors, liposomes, and plasmids. The host cell is preferably a eukaryotic cell capable of performing post-translational modifications of immunoglobulins or their fragments.

The invention also provides a method of generating a population of human monoclonal antibodies that specifically bind to antigens representative of a specific cell type. The method involves: (a) providing an isolated population of human lymphocytes comprising a plurality of non-transformed human B lymphocytes; (b) selecting the non-transformed human B lymphocytes that specifically bind to cells of the specific type; and (c) culturing the B lymphocytes of (b) under conditions favorable for B cell proliferation to yield a plurality of non-transformed B cell clones, thereby generating a population of human monoclonal antibodies exhibiting binding specificity to antigens representative of the specific cell type.

In one aspect of this embodiment, the method further comprises: (d) isolating a population of polynucleotides comprising sequences encoding the antigen-binding fragments of the heavy or light chains of the population of human monoclonal antibodies from the plurality of non-transformed B cell clones; and (e) expressing the polynucleotides to yield a population of polypeptides of the human monoclonal antibodies or the antigen-binding fragments thereof.

Further provided is the isolated population of polynucleotide and the polypetides encoded thereby. In a preferred embodiment, at least one polypeptide of the population is conjugated to a chemically functional moiety. A preferred moiety is selected from the group consisting of signal peptides, agents that enhance immunologic reactivity, agents that facilitate coupling to a solid support, vaccine carriers, bioresponse modifiers, toxins, detectable labels, or drugs.

Also embodied in this invention is a population of human monoclonal antibodies generated by any of the invention methods disclosed herein.

MODE(S) FOR CARRYING OUT THE INVENTION

Figure 1:
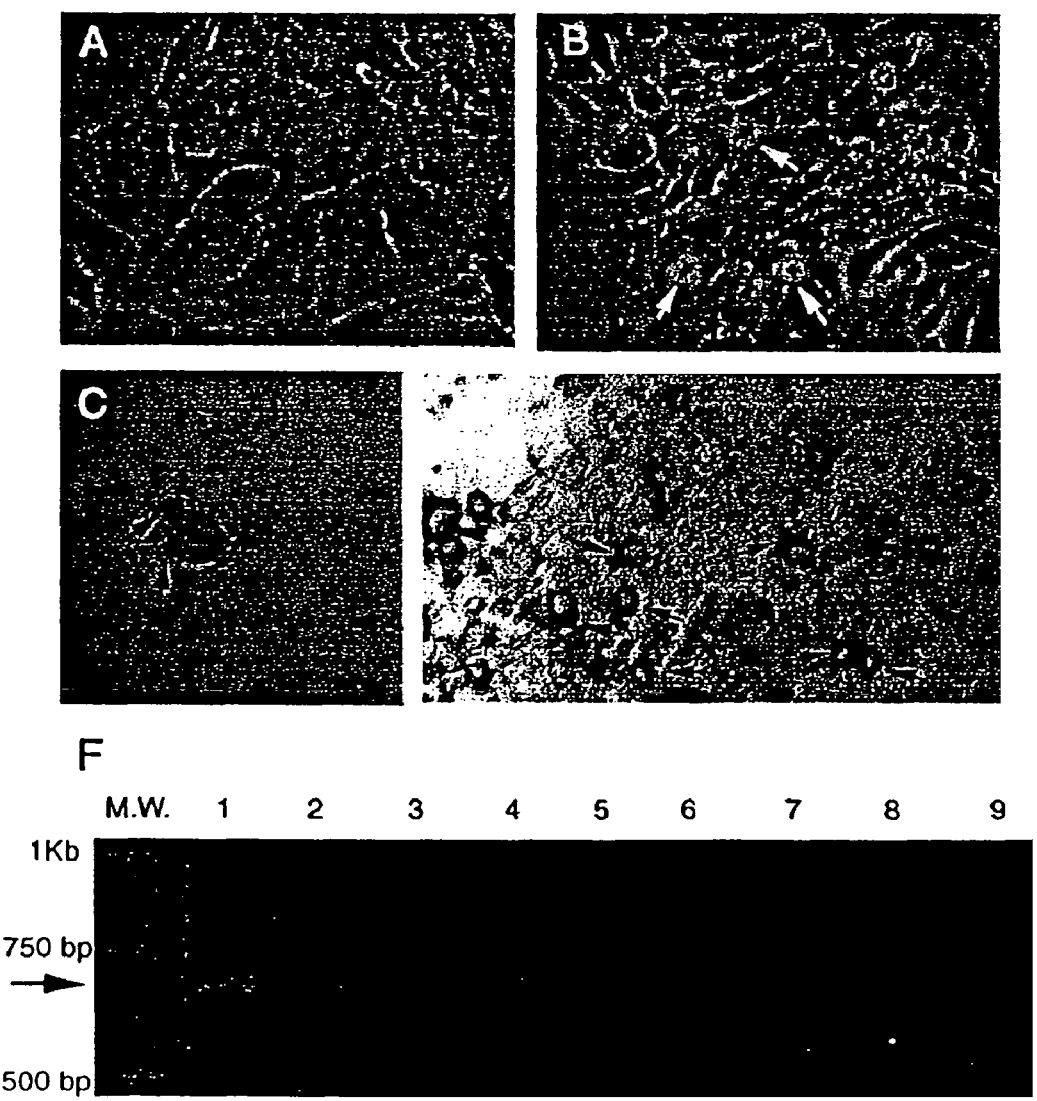
FIG. 1. A: Microphotograph of human fetal ovarian epithelial cell monolayer prior to binding to lymphocytes. B: Microphotographs of lymphocytes bound to human fetal ovarian epithelial cell monolayer (pointed by arrows). C: Black and white microphotograph of B cells bound to a human fetal ovarian epithelial cell, the arrows point to the B cells stained by anti-kappa light chain immunohistochemistry. D. Color micrograph of an anti-kappa light chain stained B cell colony after 6 days culture. E. Agrose gel analysis of PCR products showed light chain cDNA fragment (pointed by the arrow) amplified from expanded B cell colonies. Lanes 1 to 9 represent 9 different colonies.
Figure 2:
FIG. 2. A: Microphotograph of a B cell colony expanded from B cell selected against human fetal ovarian epithelial cell line. The B cells were stained with anti-kappa light chain antibody (pointed by green arrows). Note the B cells were still bound to the target cells (pointed with black arrows). B: Microphotograph of anti-kappa light chain immunocytochemical detection of COS cells expressing kappa light chain after transfected with pTargeT plasmids containing cDNA inserts that had been amplified from an in vitro expanded specific B cell colony.
Figure 3:
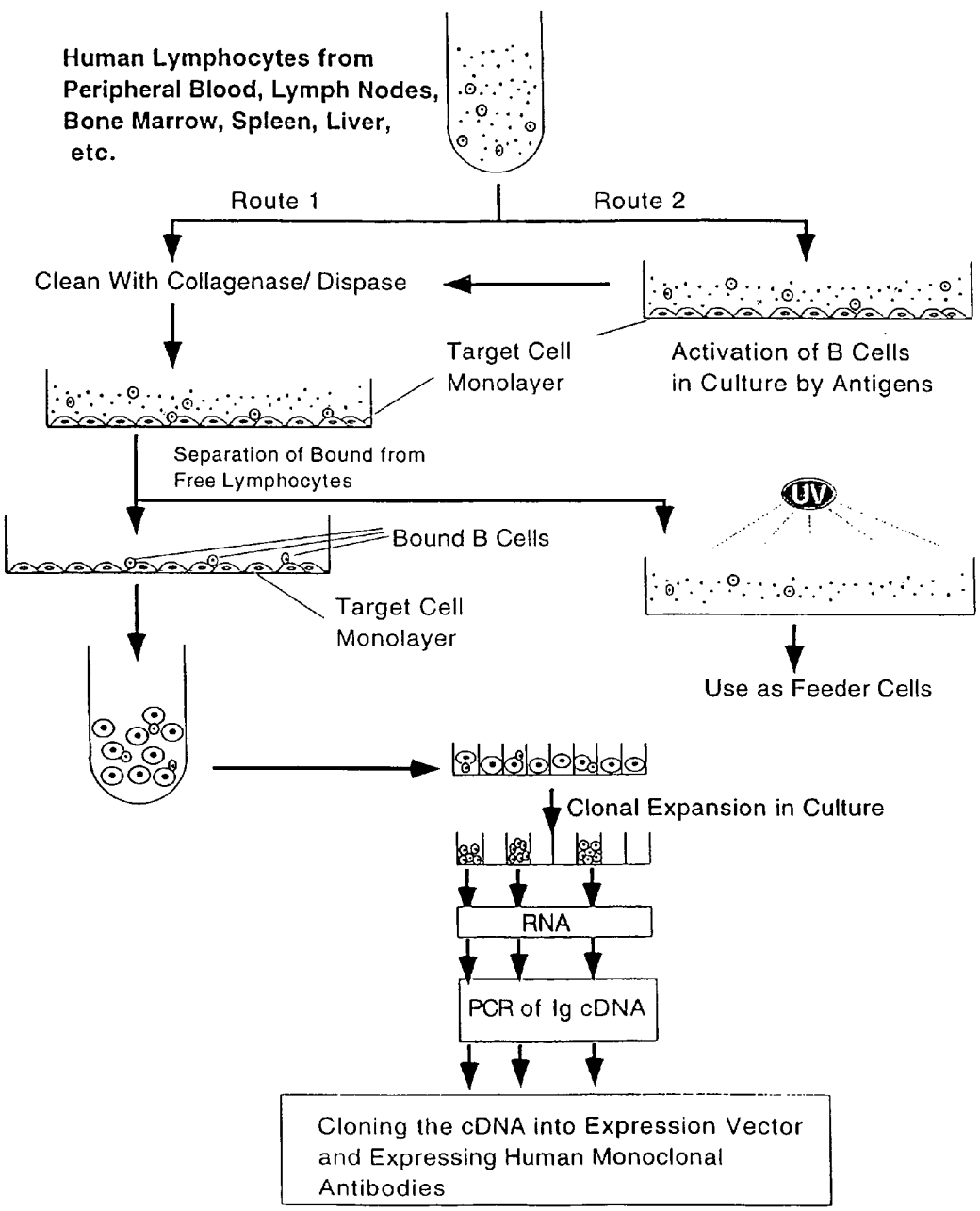
FIG. 3: A flow chart delineating a preferred invention process of generating human monoclonal antibodies.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

DEFINITIONS

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

The term "antibodies" or as used herein refers to immunoglobulin molecules and antigen-binding portions of immunoglobulin molecules, i.e., molecules that contain an antigen binding site which specifically binds ("immunoreacts with") an antigen. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including but not limited to Fab fragment(s), and Fv fragment. It has been shown that the antigen-binding function of an antibody can be performed by fragments of a naturally-occurring antibody. These fragments are also termed "antigen-binding fragments". Examples of binding fragments encompassed within the term "antigen-binding fragments" include but are not limited to (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544-546) which consists of a VH domain; (v) an isolated complimentarity determining region (CDR); and (vi) an F(ab')2 fragment, a bivalent fragment comprising two Fab fragments linked by a disulfide bridge at the hinge region. Furthermore, although the two domains of the Fv fragment are generally coded for by separate genes, a synthetic linker can be made that enables them to be made as a single protein chain (known as single chain Fv (scFv); Bird et al. (1988) *Science* 242:423-426; and Huston et al. (1988) *PNAS* 85:5879-5883) by recombinant methods. Such single chain antibodies are also encompassed within the term "antigen-binding fragments". Preferred antibody fragments are those which are capable of crosslinking their target antigen, e.g., bivalent fragments such as $F(ab')_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen.

Antibodies can be fragmented using conventional techniques as described herein and the fragments screened for utility in the same manner as described for whole antibodies. An Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab fragments can be prepared by proteolytic digestion of substantially intact immunoglobulin molecules with papain using methods that are well known in the art. However, a Fab fragment may also be prepared by expressing in a suitable host cell the desired portions of immunoglobulin heavy chain and immunoglobulin light chain using methods disclosed herein or any other methods known in the art.

An Fv fragment of an immunoglobulin molecule is a multimeric protein consisting of the immunologically active portions of an immunoglobulin heavy chain variable region and an immunoglobulin light chain variable region covalently coupled together and capable of specifically combining with an antigen. Fv fragments are typically prepared by expressing in suitable host cell the desired portions of immunoglobulin heavy chain variable region and immunoglobulin light chain variable region using methods described herein and/or other methods known to artisans in the field.

An antibody of the invention is further intended to include bispecific and chimeric molecules having a desired binding portion. Also encompassed within the term "antibodies" are vertebrate antibodies, hybrid antibodies or chimeric antibodies.

The term "monoclonal antibody" as used herein refers to an antibody composition having a substantially homogeneous antibody population. It is not intended to be limited as regards to the source of the antibody or the manner in which it is made. Monoclonal antibodies are highly specific, being directed against a single antigenic site. In contrast to conventional (polyclonal) antibody preparations which typically include different antibodies directed against different determinants (epitopes), each monoclonal antibody is directed against a single determinant on the antigen.

The term "human" as applied to a monoclonal antibody or its antigen-binding fragment refers to an antibody composition that is isolated from a human B-cell as discussed herein or recombinantly prepared by expressing polynucleotides encoding the monoclonal antibody or antigen-binding fragment thereof.

"A population of monoclonal antibodies" refers to a plurality of heterogeneous monoclonal antibodies, i.e., individual monoclonal antibodies comprising the population may recognize antigenic determinants distinct from each other.

An antibody "specifically binds" to an antigen if it binds with greater affinity or avidity than it binds to other reference antigens including polypeptides or other substances.

"Antigen" as used herein means a substance that is recognized and bound specifically by an antibody. Antigens include but are not limited to peptides, proteins, glycoproteins, polysaccharides and lipids; portions thereof and combinations thereof.

The term "immunogen" is commonly known to artisans in the field. It is an antigen capable of stimulating generation of antigen-specific antibodies by B lymphocytes when injected into a suitable host, or used for in vitro immunization of B cells. Compounds may be rendered immunogenic by many techniques known in the art, including crosslinking or conjugating with a carrier to increase valency, mixing with a mitogen to increase the immune response, and combining with an adjuvant to enhance presentation.

The term "heterologous" as applied to a cell used for in vitro immunization of B cells means that the cell is derived from a genotypically distinct entity from the recipient B cells. For example, a heterologous cell may be derived from a different species or a different individual from the same species as the recipient cell. An embryonic cell derived from an individual of one species is heterologous to an adult of the same species. Likewise, a heterologous polynucleotide or antigen is a molecule absent in the receipt B cell or structurally distinct from the counterpart expressed in the receipt cell.

A cell is of "ectodermal", "endodermal" or "mesodomal" origin, if the cell is derived, respectively, from one of the three germ layers—the ectoderm, the endoderm, or the mesoderm of an embryo. The ectoderm is the outer layer that produces the cells of the epidermis, and the nervous system. The endoderm is the inner layer that produces the lining of the digestive tube and its associated organs, including but not limited to pancreas and liver. The middle layer, mesoderm, gives rise to several organs (including but not limited to heart, kidney, gonads), connective tissues (e.g., bone, muscles, tendons), and the blood cells.

"Lymphocytes" as used herein, are cells that specifically recognize and respond to non-self or self antigens, and are responsible for development of specific immunity. Included within "lymphocytes" are B lymphocytes and T lymphocytes of various types.

The terms "medium", "cell culture medium" and "culture medium" are used interchangeably. The terms refer to the aqueous environment in which eukaryotic or prokaryotic cells are grown in culture. The medium comprises the physicochemical, nutritional, and hormonal environment. The cell culture medium is "serum-free", when the medium is essentially free of serum from any mammalian source, (e.g. sera from fetal bovine, horse, human, rabbit). By "essentially free" is meant that the cell culture medium comprises between about 0-5% serum, preferably between about 0-1% serum and most preferably between about 0-0.1% serum.

A "defined medium" refers to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cystine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

A "mitogenic agent" or "growth factor" is a molecule which stimulates mitosis of the mammalian cells. Generally, the mitogenic agent or growth factor enhances survival and proliferation of mammalian cells in cell culture and is a polypeptide. The mitogenic polypeptide can be a "native" or "native sequence" polypeptide (i.e. having the amino acid sequence of a naturally occurring growth factor) regardless of the method by which it is produced (e.g. it can be isolated from an endogenous source of the molecule or produced by synthetic techniques including recombinant techniques), or a variant or mutant thereof. Preferably, the mitogenic polypeptide has the same amino acid sequence as a growth factor derived from a human, or a fragment thereof. Non-limiting examples include activators of one or more members of the erbB receptor family; agents which elevate cAMP levels in the culture medium (e.g. forskolin, cholera toxin, cAMP or analogues thereof); adhesion molecules such as neural cell adhesion molecule (N-CAM), laminin or fibronectin; progesterone; neurotrophic factors such as bone-derived neurotrophic factor (BDNF) and ciliary neuronotrophic factor (CNTF); neurotrophin-3, -4, -5, or -6(NT-3, NT-4, NT-5, or NT-6); or a nerve growth factor such as NGF-beta; platelet-derived growth factor (PDGF); fibroblast growth factor such as acidic FGF (aFGF) and basic FGF (bFGF); vascular endothelial growth factor (VEGF); transforming growth factor (TGF) such as TGF-alpha and TGF-beta, including TGF-beta 1, TGF-beta 2, TGF-beta 3; TGF-beta 4, or TGF-beta 5; insulin-like growth factors, including IGF-I, IGF-IL and des (1-3)-IGF-I (brain IGF-I); insulin-like growth factor binding proteins; and hormones such as estrogen, testosterone, thyroid hormone, insulin and any of those mitogens listed in Table 8.2 at pages 138-139 of Mather, J. P. and Roberts, P. E. (1998) "Introduction to Cell and Tissue Culture", Plenum Press, New York.

A "cytokine," as used herein, refers to any of a variety of intercellular signaling molecules (the best known of which are involved in the regulation of mammalian somatic cells). A number of families of cytokines, both growth promoting and growth inhibitory in their effects, have been characterized including, for example: interleukins (such as IL-1.alpha., IL1.beta., IL-2, IL-3, IL4, IL-5, IL-6, IL-7, IL-8, IL-9 (P40), IL-10, IL-11, IL-12, IL-13, IL-14, and IL-15); CSF-type cytokines such as GM-CSF, G-CSF, M-CSF, LIF, EPO, TPO ("thrombopoietin"), TNF-α, and TNF-β); interferons (such as IFN-α, IFN-β, IFN-γ); cytokines of the TGF-.beta. family (such as TGF-β1, TGF-β2, TGF-β3, inhibin A, inhibin B, activin A, activin B); growth factors (such as EGF, VEGF, SCF ("stem cell factor" or "steel factor"), TGF-α, aFGF, bFGF, KGF, PDGF-A, PDGF-B, PD-ECGF, INS, IGF-I, IGF-II, NGF-β; α-type intercrine cytokines (such as IL-8, GRO/MGSA, PF-4, PBP/CTAP/βTG, IP-10, MIP-2, KC 9E3); and β-type intercrine cytokines (such as MCAF, ACT-2/PAT 744/G26, LD-78/PAT 464, RANTES, G26, 1309, JE, TCA3, MIP-1α, B, CRG-2); and chemotactic factors (such as NAP-1, MCP-1, MIP-1α, MIP-1β, MIP-2, SISβ, SISδ, SISε, PF-4, PBP, γIP-10, MGSA). A number of other cytokines are also known to those of skill in the art. The sources, characteristics, targets and effector activities of these cytokines have been described and, for many of the cytokines, the DNA sequences encoding the molecules are also known; see, e.g., R. Callard & A. Gearing, *The Cytokine facts Book* (Academic Press, 1994), and the particular publications reviewed and/or cited therein, which are hereby incorporated by reference in their entirety. As referenced in catalogs such as *The Cytokine Facts Book*, many of the DNA and/or protein sequences encoding such cytokines are also generally available from sequence databases such as GENBANK® (DNA); and/or SWISSPROT (protein). Typically, cloned DNA encoding such cytokines will already be available as plasmids, although it is also possible to synthesize polynucleotides encoding the cytokines based upon the published sequence information. Polynucleotides encoding the cytokines can also be obtained using polymerase chain reaction (PCR) methodology, as described in the art. See, e.g., Mullis & Faloona, *Met. Enzymology,* 155:355 (1987). The detection, purification, and characterization of cytokines, including assays for identifying new cytokines effective upon a given cell type, have also been described in a number of publications as well as the references referred to herein. See, e.g., *Lymphokines and*

*Interferons*, 1987; and DeMaeyer, E., et al., "Interferons and Other Regulatory Cytokines," (John Wiley & Sons 1988).

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA T any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "recombinant" polynucleotide means a polynucleotide of genomic, cDNA, semisynthetic, or synthetic origin which either does not occur in nature or is linked to another polynucleotide in a nonnatural arrangement.

A "nucleotide probe" refers to a polynucleotide used for detecting or identifying its corresponding target polynucleotide in a hybridization reaction.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

A "gene" refers to a polynucleotide containing at least one open reading frame that is capable of encoding a particular protein after being transcribed and translated.

As used herein, the term "isolated" means separated from constituents, cellular and otherwise, in which the polynucleotide, peptide, polypeptide, protein, antibody, or fragment thereof, are normally associated with in nature. As is apparent to those of skill in the art, a non-naturally occurring polynucleotide, peptide, polypeptide, protein, antibody, or fragment thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart.

Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product". If the polynucleotide is derived from genomic DNA, expression may include splicing of the mRNA in an eukaryotic cell.

"Differentially expressed", as applied to nucleotide sequence or polypeptide sequence in a subject, refers to overexpression or under-expression of that sequence when compared to that detected in a control. Underexpression also encompasses absence of expression of a particular sequence as evidenced by the absence of detectable expression in a test subject when compared to a control.

A "gene delivery vehicle" is defined as any molecule that can carry inserted polynucleotides into a host cell. Examples of gene delivery vehicles are liposomes, viruses, such as baculovirus, adenovirus and retrovirus, bacteriophage, cosmids, plasmids, fungal vectors and other recombination vehicles typically used in the art which have been described for expression in a variety of eukaryotic and prokaryotic hosts, and may be used for gene therapy as well as for simple protein expression.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions.

"Expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A "ligand" refers to a molecule capable of being bound by the ligand-binding domain of a receptor. The molecule may be chemically synthesized or may occur in nature. A ligand may be an "agonist" capable of stimulating the biological activity of a receptor, or an "antagonist" that inhibits the biological activity of a receptor.

"Cell surface receptors" or "surface antigens" are molecules anchored on the cell plasma membrane. They constitute a large family of proteins, glycoproteins, polysaccharides and lipids, which serve not only as structural constituents of the plasma membrane, but also as regulatory elements governing a variety of biological functions.

As used herein, "membrane proteins" include peripheral and integral membrane polypeptides that are bound to any cellular membranes including plasma membraries and membranes of intracellular organelles.

The terms "cytosolic", "nuclear" and "secreted" as applied to cellular proteins specify the extracellular and/or subcellular location in which the cellular protein is mostly localized. Certain proteins are "chaperons", capable of translocating back and forth between the cytosol and the nucleus of a cell.

"Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radioactive decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

As used herein, the term "antigen-presenting cell" refers to a cell that expresses an antigen of interest to which a human monoclonal antibody is raised by the methods of the present invention. The antigen is preferably expressed on the cell surface. The antigen may be native to the cell, or heterologous to the cell as its expression is under the control of an exogenously introduced polynucleotide.

"Bi-specific antibodies". A monoclonal antibody or antibody fragment may be incorporated into a bi-specific recombinant peptide as described, for example, by Greenman et al. (Greenman, J., et al., Mol. Immunol. (England) 28 (11):1243-54 (1991). In this example, a bi-specific $F(ab')_2$ was constructed, comprising two F(ab') joined by a thioether linkage. Bi-specific antibodies may also be obtained when two whole antibodies are attached. Another way to obtain bi-specific antibodies is by mixing chains from different antibodies or fragments thereof. In this manner the "left" branch of the bi-specific antibody has one function while the "right" branch has another.

"Microorganisms" are biological entities invisible to the unaided eye. These entities constitute a large phylum of lower organisms including but are not limited to bacteria, fungi, viruses, and microplasma.

Generation of Human Monoclonal Antibody Immunoreactive with a Desired Antigen

Preparation of Non-Transformed Human B Cells:

The non-transformed human B cells that can be employed in the present invention are widely distributed in lymphocytes from the peripheral blood, lymph nodes, spleen, liver, bone marrow, umbilical cord, or other issues of a human being. While there is no particular restriction as to the source of the human B cells, peripheral blood is preferably employed because it is readily obtainable (e.g. from commercial sources or appropriate donors) and contains an ample amount of B cells. Whereas any individual who generates B cells in his or her body is a candidate donor, those who have previously been exposed to the antigen of particular interest, and are likely to contain the immunized B cells are preferred donors.

Extraction of lymphocytes contained in the human peripheral blood or other body tissues can be performed according to any of the methods well known in the art. Representative methodologies are density gradient centrifugation and immunoaffinity depletion of non-B lymphocytes. When performing density gradient centrifugation, samples such as the peripheral blood are typically diluted with an appropriate isotonic medium which is preferably free of calcium and/or magnesium ions. The diluted blood is then loaded onto a suitable separation medium to effect separation of the peripheral blood lymphocytes (PBL) from the red blood cells and platelets when subjected to centrifugation. Commonly employed separation media include but are not limited to FICOLL® (available from Pharmacia, Sweden), LYMPHOPREP® (density: 1.077 g/ml, Nycomed Pharma As, Oslo, Norway) and Percoll® (Pharmacia, Sweden). Upon completion of centrifugation, the PBLs may be aspirated from the interface between the serum and the separation medium. The purified PBLs may be stored at low temperature (e.g. in liquid nitrogen) until use.

An alternative method of preparing lymphocytes enriched for B cells involves the removal of T-lymphocytes by resetting with 2-aminoethylisothio uronium bromide hydrobromide (AET)-treated sheep erythrocytes. The process generally proceeds with mixing the PBLs with treated erythrocytes, followed by separating the B cells from T lymphocytes on a separation medium by means of centrifugation.

Further enrichment for B cells may be accomplished by affinity chromatography, panning on monoclonal antibody coated culture vessels, magnetic separation techniques, or a cell sorting means (e.g. FACS) that effect in either retention of B cells or depletion of T-lymphocytes. Both methods employ detecting agents capable of differentiating the two types of lymphocytes. Such detecting agents include but are not limited to peptides, and glycoproteins which specifically bind to cell surface molecules that are preferentially expressed, if not exclusively expressed, in one but not both types of lymphocytes. A variety of T cell specific marker molecules are known in the art. Non-limiting examples of T cell specific marker molecules include TCR/CD3 complex, CD2, CD4, CD8, and CD28. Non-limiting example of B cell specific marker molecules include CD 19, CD20, CD21, HLA-DR, and B cell antigen 36 kD. In preparing a lymphocyte composition comprising a plurality of non-transformed B cells, any one of the aforementioned approaches, or procedures modified therefrom, can be performed either singly or in any combination.

The resulting enriched and/or sorted B cell population can be employed for screening B cells that exhibit specific binding to a desired antigen or, optionally, subjected to in vitro immunization/activation with the desired antigen prior to such screening procedure. In vitro immunization/activation of B cells is particularly advantageous in (a) stimulating the production of antigen-specific B cells; and (b) generating B cells capable of recognizing self-antigens or antigens to which the lymphocyte donor has never been exposed and/or has failed to elicit a strong immune response.

In Vitro Immunization/Activation of Non-Transformed Human B Cells:

The procedures of in vitro immunization of B cells are generally in keeping with established and conventional techniques of B cell activation. The process involves contacting a population of non-transformed human B cells with a desired antigen under conditions favorable for a specific binding of B cells to the desired antigen. Whereas any means resulting in a stable and specific association of B cells with the desired antigen can be employed, immunization of B cells is preferably performed by co-culturing B cells with the antigen in an "immunization medium". In general, the antigens are immobilized on the solid substrate where the B cells are grown. In certain embodiments of the present invention, the desired antigens are presented by a monolayer of cells expressing such antigens. Any cells capable of growth in culture are candidate cells for antigen presentation. Where desired, exogenous polynucleotides capable of directing the expression of the desired antigens can be introduced into the antigen-presenting cells.

The immunization medium suitable for the present invention supports B lymphocyte survival in vitro, maintains its morphology, capacity to metabolize and potentially, capacity of the cell to differentiate. It is preferable to employ a defined medium comprising nutritional and hormonal requirements necessary for the survival and/or growth of B cells in culture such that the components of the medium are known. The general parameters governing mammalian cell survival in vitro are known in the art. Physiochemical parameters which may be controlled in cell culture systems are, e.g., pH, $CO_2$, temperature, and osmolarity. The nutritional requirements of B cells are usually provided in standard media formulations developed to provide an optimal environment. Nutrients can be divided into several categories: amino acids and their derivatives, carbohydrates, sugars, fatty acids, complex lipids, nucleic acid derivatives and vitamins. Apart from nutrients for maintaining cell metabolism, generally B cells also require one or more hormones or mitogens from at least one of the following groups: steroids, prostaglandins, growth factors, pituitary hormones, lectins, adjuvant peptides, and peptide hormones to proliferate in serum-free media (Sato, G. H., et al. in "Growth of Cells in Hormonally Defined Media", Cold Spring Harbor Press, N.Y., 1982). In addition to hormones, B cells may require transport proteins such as transferrin (plasma iron transport protein), ceruloplasmin (a copper transport protein), and high-density lipoprotein (a lipid carrier) for survival and growth in vitro.

The immunogens that can be employed in the process of in vitro activation are compositions expected to induce antibody production in a human B cell. A diverse variety of immunogens are known in the art. Non-limiting examples of various types of immunogens include biological or chemical compounds such as a simple or complex organic or inorganic molecule, a peptide, a protein, a glycoprotein, a polynucleotide (e.g. antisense oligonucleotide), a ribozyme, and their derivatives. A vast array of compounds can be synthesized, for example polymers, such as polypeptides, and polynucleotides, and synthetic organic compounds based on various core structures, and these are also included in the term "chemical compounds". In addition, various natural sources such as plant or animal extracts, and the like can be used for immunization.

To generate human monoclonal antibodies that bind antigens representative of a specific cell type, tissues composed of such cell type, cultures of tissues or cells derived therefrom and the progeny thereof, sections or smears prepared from any of these sources, as well as samples of purified antigens can be employed. In addition, membrane extracts, cytosolic extracts, or whole cells of a particular cell type that are enriched with the antigen of interest can also be used for the in vitro immunization. Of particular interest are the cells differentially expressing (over-expressing or under-expressing) a disease-causing gene, cells arresting at various cell-cycle points ($G_0$, $G_1$, $G_2$, M, or S phase), cells of different developmental stages (adult or embryonic) or developmental origins (e.g. ectodermal, endodermal or mesodermal), and cells being infected with one or more types of micro-organisms including bacteria, fungi and viruses. As is apparent to one skilled in the art, various cell lines may be established according to conventional tissue culture techniques. They may also be obtained from public or private repositories. The largest depository agent is American Type Culture Collection (http://www.atcc.org), which offers a diverse collection of well-characterized cell lines derived from a vast number of organisms and tissue samples.

The antigens representative of a cell type of interest may fall under one or more the following categories: receptor ligands, secreted proteins, cell surface receptors, cytosolic proteins, or nuclear proteins. Of particular interest are the antigens exhibiting restricted tissue, cell-type or subcelluar distribution patterns. Within these sub-categories, the antigens with major diagnostic and/or therapeutic potential are those involved in a specific biological process, including but not limited to cell cycle regulation, cell differentiation, apoptosis, chemotaxis, cell motility and cytoskeletal rearrangement. Other types of antigens of therapeutic potential include those associated with a particular disease or with a specific disease stage. Such antigens include but are not limited to those associated with autoimmune diseases, obesity, hypertension, diabetes, neuronal and/or muscular degenerative diseases, cardiac diseases, endocrine disorders, any combinations thereof.

For production of monoclonal antibodies directed to cell-surface antigens of a specific cell type, it is desirable to immunize the non-transformed B cells with viable and intact cells of that type, preferably with those cells whose surfaces are free of serum. Immunization with cells that have been propagated in a serum-supplemented medium may have pronounced disadvantages. Serum is an extremely complex mixture of many small and large biomolecules with undefined activities. Numerous kinds of these serum biomolecules are known to adhere to the cell surfaces. These biomolecules include but are not limited to transfer proteins (e.g. albumin), attachment and spreading factors (e.g. collagen and fibronectin), and various kinds of serum lipids. Adsorption of these exogenous molecules to the cell surface not only results in the generation of antibodies cross-reacting with molecules unrepresentative of the specific cell type, but can also mask presentation of the native antigens, and thus further undermines the "representativeness" of the resulting monoclonal antibody pool.

To ensure that the cell surfaces are free of serum, cells are typically grown in a defined medium that lacks serum but is supplemented with hormones, growth factors or any other factors necessary for the survival and/or growth of a particular cell type. Procedures for formulating a defined medium for a specific cell type is well established in the art and hence are not detailed herein. (Barnes, D. and Sato, G. (1980) *Anal. Biochem.*, 102:255; Mather, J. P; and Roberts, P. E. (1998) "Introduction to Cell and Tissue Culture", Plenum Press, New York).

Selection of Non-Transformed B Cells that Bind Specifically to a Desired Antigen:

Prior to screening for B cells exhibiting the desired antigen-binding specificity, the enriched B cell population or the activated B cells are pre-treated with dissociation agents that disrupt cell aggregates and remove the bound antigens from the B cell surfaces. When applying the dissociation agents, precautions are taken to maintain B cell membrane integrity and preserve the cell membrane components. Unlike the traditional method of dissociating the anchored cells or cell layers by the action of strong proteolytic enzymes such as serine proteinase, trypsin, non-transformed B cells of the present invention are typically removed from the culture substrates by agents that minimize damages to the cell surface molecules. These agents include but are not limited to collagenases, dispases, and neutral proteinases. Treatment of B cells with these agents mostly result in disruption of aggregates while preserving the cell surface immunoglobulins. The period of treatment required to dissociate the cell aggregates or detach the cells anchored on a solid substrate can vary depending on the proteinase enzyme chosen, but will normally be a period of about 3 minutes to 60 minutes, and preferably about 15 minutes to 30 minutes. The enzymatic treatment is normally carried out at room temperature to about 37° C. Excess enzymes can be removed by gentle washing with buffers having pH and salt concentrations in the physiological range, or serum-free media that are routinely prepared by one skilled in the art.

The subsequent selection of B cells immunoreactive with the desired antigens involves the following steps: (a) contacting a population of human lymphocytes comprising B cells with the desired antigen under conditions favorable for specific binding of B lymphocytes to the desired antigen; and (b) separating the unbound B lymphocytes from the B lymphocytes bound to the desired antigen. The process typically proceeds with layering the antigens onto a solid substrate, followed by plating B lymphocytes over the layer of antigens. The B lymphocytes are then allowed to bind to the antigens under physiological conditions, wherein the pH is maintained between 6 and 8 and the temperature is between about 20° to 40° C. The unbound B lymphocytes are removed by washing, aspiration or any other suitable means.

A variation of this process is subtractive selection. For example in selecting B cells specifically binding to colon cancer cells, a repertoire of human lymphocytes are incubated with a monolayer of normal cells. Those B-cells that display antibodies against normal colon cells will bind to the cell monolayer. The unbound B cells are collected and incubated with a monolayer of colon cancer cells. This time, only those B-cells that produce monoclonal antibodies specifically recognizing colon cancer cells will bind and the non-specific B-cells can be washed away.

When intact cells expressing the desired antigens are employed in the selection process, typically a monolayer of viable cells grown in a serum free medium at about 5% to 100% confluence are seeded onto a solid phase substrate. The substrate on which the antigen-presenting cells are seeded may be manufactured from a variety of materials. The choice of substrates is determined largely by the type of cells. Most cells can be propagated on a substrate made of e.g., glass, plastic or ceramic material. For certain cell types, such as neurons, epithelial and muscle cells, substrates precoated with charged substances that enhance cell attachment and spreading are preferred. Commonly employed coating materials include biological substrates that bear a net positive charge. Non-limiting examples of biological substrates include extracellular matrix/adhesion proteins such as laminin, fibronectin, collagen, or synthetic polypeptide such as polylysine. A variety of non-biological substrates such as membranes made of nitrocellulose, nylon, polytetrafluoroethylene, or any other implant materials can also be used to support growth of cells in a serum-free medium.

After seeding a monolayer of the antigen-presenting cells, a suspension of non-transformed human B lymphocytes is then added to the cell monolayer and incubated at about 37° C. for an appropriate amount of time. The incubation period required to allow B cells to bind to their specific antigen through specific recognition of their surface immunoglobulins can vary depending on the relative abundance of the B lymphocytes and the antigen-presenting cells. It will normally be a period of about 10 minutes to 120 minutes, and preferably about 30 minutes to 60 minutes. Upon completion of incubation, the unbound B lymphocytes are removed from the monolayer of antigen-presenting cells by washing with $Ca^{++}/Mg^{++}$ free buffer. The washed free B lymphocytes are collected by centrifugation and then subjected to UV irradiation. The UV treated B lymphocytes would die within 3 day in culture and are employed as feeder cells for subsequent clonal growth of the selected B lymphocytes. The remaining B cells bound to the monolayer of antigen-presenting cells are the ones expressing desired immunoglobulins on their cell surfaces. These cells are designated "selected B lymphocytes".

Clonal Expansion of Selected B Lymphocytes:

Prior to clonal expansion, the selected B lymphocytes are dissociated from the antigens using suitable means that substantially preserve the viability of the cells. A preferred way of detaching B cells from the antigens is treatment with mild proteinases as discussed above. To generate isolated colonies of the selected B cells, the dissociated cells are plated at low density in a medium that supports not only survival but also proliferation of non-transformed B cells. The culture medium suitable for clonal expansion of B cells comprises nutritional and hormonal requirements necessary for sustaining the growth of the cells for at least 1 doubling times, preferably more than 3 times, more preferably more than 5 times. As such, an isolated colony of non-transformed human B cells refers to herein as a cell cluster, comprising at least 2 progeny cells, preferably –8 progeny cells, more preferably 32 progeny cells that are derived from a single B cell with the desired antigen-binding specificity. Non-limiting exemplary culture media capable of supporting the required clonal expansion of non-transformed B cells include MEM, DMEM, RPMI, F-12 containing supplements required for cellular metabolism such as glutamine and other amino acids, vitamins, minerals and useful transport proteins such as transferrin and the like. The culture medium may also contain antibiotics to prevent contamination with yeast, bacteria and fungi. Suitable antibiotics for cell cultures include but are not limited to penicillin, streptomycin, gentamicin, and kanamycin. Whereas the medium may optionally contain 1-10% serum derived from bovine, equine, horse, chicken and the like, it is preferable to culture the cells with defined medium supplemented with at least one growth factor or mitogen described herein. Preferred mitogens include pokerweed mitogen, insulin, Il-2, IL-4, IL6, IL10, anti-CD40/CD40 ligand. Growth factors are usually added to the culture medium at concentrations ranging between about 1 pg/ml to 0.1 mg/ml. Concentrations between about 1 ng to 10 ug/ml are usually sufficient. Simple titration experiments can be easily performed to determine the optimal concentration of a particular growth factor.

In addition to the aforementioned cell culture factors, feeder cells may be employed to promote clonal expansion of non-transformed human B cells. As used herein, "feeder cells" are accessory cells that provide co-stimulating functions in conjunction with B cell propagation. Feeder cells such as peripheral blood mononuclear cells can be obtained by techniques known in the art, for examples by leukaphoresis, which is a standard medical procedures with minimal risks (see, e.g., Weaveer et al., (1993) *Blood* 82: 1981-1984); and these feeder cells can be stored by cryopreservation in liquid nitrogen until use. Other illustrative types of feeder cells are EBV-transformed lymphoblastoid cells (Crossland et al. (1991) *J. Immunol.* 146: 4414-20), bone marrow stromal cells, liver stromal cells, and 3T3 fibroblast cell lines. A preferred type of feeder cells are lymphocytes incapable of binding to the desired antigen, harvested as the unbound, free lymphocytes during the selection step noted above. Preferably, the ratio of feeder cells to the non-transformed B lymphocytes to be expanded is at least about 100:1, more preferably about $10^4$:1, and even more preferably about $10^6$:1.

Feeder cells of the present invention are generally prevented from undergoing mitosis. Techniques for inhibition of mitosis are well established in the art. The most common procedure is irradiation. For instance, lymphocytes can be irradiated with short UV wave having a wave length in the range of about 220 to about 290 nm (preferably at 254 nm) for approximately 30 minutes from a distance of about 5 cm to 25 cm. Peripheral blood mononuclear cells can be irradiated with gamma rays in the range of about 3,000 to 4,000 rads (preferably at about 3,600 rads). Any lymphoblastoid cells can be irradiated with gamma rays in the range of about 6,000 to 12,000 rads (preferably at about 10,000 rads). Other types of cells can also be irradiated with gamma rays in the range of about 6,000, to 12,000 rads.

Since the antigen specificity of the B cell clone is defined prior to expanding the cell in the culture system, either autologous or allogeneic feeder cells can be used to support B cell growth. The addition of allogeneic feeder cells is important in situations in which the lymphocyte donor is infected with a virus that is present in e.g. peripheral blood, that could therefore contaminate the B cell cultures. In such circumstances, the use of allogeneic feeder cells derived from an individual that is screened and deemed to be a suitable blood donor by American Red Cross criteria can be used in the culture method.

Conditions for culturing non-transformed B cell clones should be close to physiological conditions. The pH of the culture medium should be close to physiological pH, preferably between pH 6-8, more preferably between about pH 7 to 7.8, with pH 7.4 being most preferred. Physiological temperatures range between about 25° C. to 40° C. Cells are preferably cultured at temperatures between about 32° C. to about 38° C., and more preferably between about 35° C. to about 37° C.

Applying the above-described general techniques, populations of non-transformed B cell clones expressing immunoglobulins that recognize antigens representative of human fetal brain primary cell line, human fetal ovarian cell line, human lung carcinoma cell line A549, and adult human Schwann cell line, embryonic pancreatic ductal cells, have been generated.

Isolation and Expression of the Polynucleotides Encoding a Desired Human Monoclonal Antibody or Fragments Thereof The non-transformed B cell clones embodied in this invention provide specific reagents for isolating and cloning the polynucleotides encoding the human monoclonal antibody with the desired binding specificity.

Structurally, the simplest naturally occurring antibody (e.g., IgG) comprises four polypeptide chains, two heavy (H) chains and two light (L) chains inter-connected by disulfide bonds. The human antibodies constitute a large family of molecules that include several classes of immunoglobulins, such as IgD, IgG, IgA, IgM and IgE. Generally, the two types of chains are encoded by separate genes. Over the past few decades, a vast number of genes encoding a battery of human antibodies have been cloned and sequenced. Extensive sequence analyses have revealed that the immunoglobulin chains of the same class contain a highly conserved "constant region" with a variable region constituting the antigen binding site. Based on the existing sequences of various classes of immunoglobulins, a variety of recombinant DNA techniques can be employed for isolation of the immunoglobulin genes encoding the light and heavy chains of a desired immunoglobulin. Representative cloning methods including PCR, cDNA library construction and screening, homology searches in existing nucleic acid databases, or any combination thereof. Commonly employed databases include but are not limited to GenBank, EMBL, DDBJ, PDB, SWISS-PROT, EST, STS, GSS, and HTGS.

One illustrative method of isolating the immunoglobulin genes that code for the invention human monoclonal antibodies involves the steps of (a) extracting nucleic acids from a non-transformed B cell clone of the present invention; (b) synthesizing cDNA encoding either the light or heavy chain of the desired antibody or a fragment thereof; and (c) amplifying the cDNA to yield a sufficient quantity of DNA molecules for sub-cloning and/or gene expression.

Nucleic acids contained in the non-transformed B cell clone can be extracted according to standard methods in the art or the procedures exemplified herein (Example 6). For instance, DNA and RNA can be isolated using various lytic enzymes or chemical solutions according to the procedures set forth in Sambrook et al. ("Molecular Cloning: A Laboratory Manual", Second Edition, 1989), or extracted by nucleic acid binding resins following the accompanying instructions provided by manufactures. The synthesis of cDNA can be carried out by reverse transcription in conjunction with various amplification techniques. For the purpose of this invention, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and/or RNA polymerases such as reverse transcriptase.

A preferred amplification method is PCR. General procedures for PCR are taught in U.S. Pat. No. 4,683,195 (Mullis) and U.S. Pat. No. 4,683,202 (Mullis et al.). However, PCR conditions used for each application reaction may be empirically determined or estimated using a computer software program. A number of parameters influence the success of a reaction. Among them are annealing temperature and time, extension time, Mg2+ATP concentration, pH, and the relative concentration of primers, templates, and deoxyribonucleotides. Exemplified herein are conditions and specific primers for replicating the human light and heavy chains (see Example 6-7).

After amplification, the resulting polynucleotides can be detected by agarose gel electrophoresis followed by visualization with ethidium bromide staining and ultraviolet illumination. A specific amplification of an immunoglobulin gene can be verified by demonstrating that the amplified polynucleotide has the predicted size, exhibits the predicated restriction digestion patterns, or hybridizes to the correct cloned DNA sequence.

The isolated polynucleotide comprising a desired sequence can be inserted into a suitable vector, and the vector in turn can be introduced into a suitable host cell. The host cells of this invention can be used, inter alia, as repositories of genes encoding specific human monoclonal antibodies, or as vehicles for production of the antibodies. Polynucleotides can be introduced into host cells by any means known in the art. For instance, host cells can be transfected by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome.

The present invention provides a population of polynucleotides encoding chains of a population of human monoclonal antibodies that bind to antigens representative of a specific cell type. Preferably, the cells are eurkaryotic cells, more preferably mammalian cells, even more preferably human cells. Other cells of particular interest are those differentially expressing (over-expressing or under-expressing) disease-causing genes; those exhibiting cell-cycle defects (e.g. arresting at various cell-cycle points including $G_0$, $G_1$, $G_2$, M, or S phase); and those of different developmental stages (adult or embryonic) or developmental origins (e.g. ectodermal, endodermal or mesodermal).

Individual polynucleotides can be introduced into a suitable host cell using a variety of gene delivery vehicles. As used herein, gene delivery vehicles include both viral and non-viral vectors such as naked plasmid DNA or DNA/liposome complexes. Vectors are generally categorized into cloning and expression vectors. Cloning vectors are useful for obtaining replicate copies of the polynucleotides they contain, or as a means of storing the polynucleotides in a depository for future recovery. Expression vectors (and host cells containing these expression vectors) can be used to obtain polypeptides produced from the polynucleotides they contain. Suitable cloning and expression vectors include any known in the art, e.g., those for use in bacterial, mammalian, yeast and insect expression systems. The polypeptides produced in the various expression systems are also within the scope of the invention.

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins, e.g., ampicillin, neomycin, methotrexate; (b) complement auxotrophic deficiencies; or (c) supply critical nutrients not available from complex media. The choice of the proper marker gene will depend on the host cell, and appropriate genes for different hosts are known in the art. Vectors also typically contain a replication system recognized by the host.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pBR322, pMB9, ColE1, pCR1, RP4, pUC18, mp18, mp19, phage DNAs, and shuttle vectors such as pSA3 and pAT28. These and other cloning vectors are available from commercial vendors such as Clontech, BioRad, Stratagene, and Invitrogen.

Expression vectors containing the isolated human immunoglobulin genes or gene fragments are useful to obtain host vector systems to produce antibodies or antibody fragments such as antigen-binding fragments. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer. A particularly useful expression vector (system) is the baculovirus/insect system. Suitable vectors for expression in the baculovirus system include pBackPack9 (Clontech), pPbac and pMbac (Strategene). Adenoviral vectors are particularly useful for introducing genes into tissues in vivo because of their high levels of expression and efficient transformation of cells both in vitro and in vivo.

The polynucleotides can also be modified to contain a detectable marker, e.g., an enzymatic label or a radioisotope for detection of nucleic acid and/or expression of the corresponding gene(s) in a lymphocyte. A wide variety of appropriate detectable markers are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

The polynucleotides of the invention can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention. In addition, the polynucleotides may be fused with other desired sequences to augment immunological reactivity of the resulting polypeptides, or to facilitate purification of the polypeptides.

The polypeptides embodied in the present invention comprise a population of immunoglobulin chains or their fragments that are encoded by the population of polynucleotides described above. Preferred immunoglobulin fragments are those that contain portions of the sequences of a whole immunoglobulin but reserve the antigen-binding specificity. A particularly preferred antigen-binding fragment is single chain V region fragment ("scFv"). Single chain V region fragments are made by linking L and/or H chain V regions by using a short linking peptide. Bird et al. (1988) *Science* 242:423-426. Any peptide having sufficient flexibility and length can be used as a linker in a scFv. Usually the linker is selected to have little to no immunogenicity in the recipient host. An example of a linking peptide is (GGGGS)$_3$ (SEQ ID NO: 9), which bridges approximately 3.5 nm between the carboxy terminus of one V region and the amino terminus of another V region. Other linker sequences can also be used, and can provide additional functions, such as a means for attaching a drug or a solid support.

All or any portion of the H or L chain can be used in any combination. Typically, the entire V regions of an immunoglobulin are included in the scFv. For instance, the L chain V region can be linked to the H chain V region. Alternatively, a portion of the L chain V region can be linked to the H chain V region, or a portion thereof. Also contemplated are scFvs in which the H chain V region and the L chain V region are derived from different immunoglobulins. It is also possible to construct a biphasic, scFv in which one component is derived from the immunoglobulin generated by a selected B cell of the present invention, and another component is a different polypeptide, such as a T cell epitope.

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *E. coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

Expression conditions should ensure that the scFv assumes functional and, preferably, optimal tertiary structure. Depending on the plasmid used (especially the activity of the promoter) and the host cell, it may be necessary to modulate the rate of production. For instance, use of a weaker promoter, or expression at lower temperatures, may be necessary to optimize production of properly folded scFv in prokaryotic systems; or, it may be preferably to express scFv in eukaryotic cells.

The invention also encompasses human monoclonal antibodies or fragments conjugated to a chemically functional moiety. Typically, the moiety is a label capable of producing a detectable signal. These conjugated antibodies are useful, for example, in detection of the target antigens. A vast number of suitable labels are known in the art and include, but are not limited to, radioisotopes, enzymes, and luminescent compounds. The moieties can be covalently linked to the antibody, recombinantly linked, or conjugated to the antibody through a secondary reagent, such as a second antibody, protein A, or a biotin-avidin complex.

Other functional moieties include signal peptides, agents that enhance immunologic reactivity, agents that facilitate coupling to a solid support, vaccine carriers, bioresponse modifiers, and drugs. Signal peptides are short sequences usually residing at the N-terminus and direct the secretion of the proteins from a cell. Agents that enhance immunologic reactivity include, but are not limited to, bacterial superantigens. Agents that facilitate coupling to a solid support include, but are not limited to, biotin or avidin. Immunogen carriers include, but are not limited to, any physiologically acceptable buffers. Bioresponse modifiers include cytokines, particularly tumor necrosis factor (TNF), interleukin-2, interleukin-4, granulocyte macrophage colony stimulating factor and γ-interferon.

Suitable drug moieties include antineoplastic agents. These include, but are not limited to, radioisotopes, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, Taxol®, thioguanine, and uracil mustard.

Immunotoxins, including single chain molecules, can be produced by recombinant means. Production of various immunotoxins is well-known in the art, and methods can be found, for example, in "Monoclonal Antibody-toxin Conjugates: Aiming the Magic Bullet," Thorpe et al. (1982) *Monoclonal Antibodies in Clinical Medicine*, Academic Press, pp. 168-190; Vitatta (1987) Science 238:1098-1104; and Winter and Milstein (1991) *Nature* 349:293-299. Suitable toxins include, but are not limited to, ricin, radionuclides, pokeweed antiviral protein, *Pseudomonas* exotoxin A, diphtheria toxin, ricin A chain, fungal toxins such as restrictocin and phospholipase enzymes. See, generally, "Chimeric Toxins," Olsnes and Pihl, *Pharmac. Ther.* 15:355-381 (1981); and "Monoclonal Antibodies for Cancer Detection and Therapy," eds. Baldwin and Byers, pp. 159-179, 224-266, Academic Press (1985).

Uses of the Composition of the Present Invention

The polynucleotides and gene delivery vehicles of this invention have several uses. They are useful, for example, in expression systems for the production of human monoclonal antibodies and their fragments that are immunoreactive with the specific antigens. They are also useful as hybridization probes to assay for the presence of the immunoglobulin gene encoding a desired human monoclonal antibody in a biological sample. Further, the polynucleotides are useful as primers to effect amplification of desired polynucleotides. The polynucleotides of this invention may also useful in pharmaceutical compositions including vaccines and for gene therapy.

The antibodies and polypeptides embodied in this invention provide specific reagents that can be used in standard diagnostic procedures. Specifically, the antibodies or their immunoreactive fragments can be employed in immunoassays for detection of the target antigens. To perform a diagnostic method of this invention, one of the compositions of this invention is provided as a reagent to detect a target antigen in a sample with which it reacts. The target antigen is supplied by obtaining a suitable biological sample from an individual for whom the diagnostic parameter is to be measured. Relevant biological samples are cell or tissue samples suspected to contain the targets. Procedures for performing immunoassays are well established in art and hence are not detailed herein.

The human monclonal antibodies generated by the invention methods may also have utility for treatment or prevention of human diseases. The monoclonal antibodies may be used to modulate the activities of target antigens that play a central role in disease development and/or progression. For instance, a humanized anti-Her2 antibody, available commercially and under the trademark HERCEPTIN®, which selectively inhibit growth of human breast cancer cells, is now employed as a potent drug to treat tens and thousands of breast cancer patients who overexpress the breast cancer antigen Her2. Thus, the human monoclonal antibodies of this invention may also be tested for their abilities to augment or inhibit the biological activities of the target antigens.

The following examples provide a detailed description of the preparation, characterization, and use of representative monoclonal antibodies of the present invention. These examples are not intended to limit the invention in any manner.

EXAMPLES

Example 1

Isolation of Lymphocytes from Peripheral Blood

Human lymphocytes were isolated from "buffy coat" obtained from National Blood Bank. The "buffy coat" was diluted with one volume of $Ca^{++}/Mg^{++}$ free PBS. The diluted buffy coat was carefully layered onto the top of 10 ml Lymphoprep® (density: 1.077 g/ml, Nycomed Pharma As, Oslo, Norway) in each 50 ml centrifuge tube and centrifuged at 800 g for 30 minutes at 20° C. After centrifuge, the lymphocytes had formed a white band above the Lymphoprep® solution when red blood cells precipitate at the bottom of the tube. The lymphocytes were collected into a fresh centrifuge tube and washed twice with PBS. The yield of lymphocytes of each preparation was between $3-5 \times 10^8$ cells. The lymphocytes isolated were used for specific B-cell selection either immediately or after culture with antigen/antigens of interest for 24-8 hours.

Example 2

In Vitro Immunization/Activation of B Lymphocytes by Antigens of Interest

By this method, specific B-cells were activated by antigens before selection. The lymphocytes isolated above were diluted in in vitro immunization medium (F12/DMEM supplemented with 10 µg/ml insulin, 10 µg/ml transferrin, 10 nM Selenium, 3 nM progesterone, 2.5 µg/ml pokerweed mitogen and 10 ng/ml IL-2) at a density of $10^7$ cells/ml. The cells were then plated onto a monolayer of cells that we would develop monoclonal antibodies to. We used human fetal brain primary cell line, human fetal ovarian cell line, human lung carcinoma cell line A549, and adult human Schwann cell line.

Example 3

Selection for Non-Transformed B Cells with Desired Antigen-Binding Specificity

Prior to selection of B-lymphocytes against specific antigens, the lymphocytes were incubated with 0.25% collagenase/dispase in serum free medium for 30 minutes to clean the lymphocyte cell surface. This step is important for reducing cell aggregation during selective binding of B-cells and removing the bound antigens from the B-cell surface especially for the cells that had been exposed to the antigens during in vitro immunization. The cells were then washed twice with serum free medium to remove residual enzymes. The cleaned cells were counted, diluted in serum free medium to a density of $10^7$ cells/ml ready for panning.

The selection process proceeded with seeding a monolayer cells at about 5% to 100% of confluence in a serum free medium. Lymphocyte suspension was added to the monolyer and incubated at 37° C. for 1 hour for B cells to bind to their specific antigen through specific recognition of their surface immunoglobulins. Gentle agitation of the culture was performed to mix the cells at an interval of about 15 minutes. After the incubation, the free lymphocytes were washed away from the monolayer of target cells with $Ca^{++}/Mg^{++}$ free PBS and were collected and centrifuged at 1500 rpm for 10 minutes. The free lymphocytes were killed by exposure to UV irradiation for 35 minutes with short wave UV (254 nm) for 30 minutes with UVGL-58 at a distance of 10 cm. The UV treated lymphocytes would die within 3 day in culture and used as feeder cells for clonal growth of the selected B lymphocytes. The B cells remained bound to the monolayer of target cells through washes were the B cells with specific immunoglobulin on their cell surface, designated as "selected B lymphocytes". The cells were then released from the culture plates together with the target monolyer cells by incubation in PBS with 0.02% EDTA at 37° C. for 15 minutes. The cells collected and washed with serum free medium.

Example 4

Clonal Expansion of Selected B-Cells

The selected B cells were plated in 96 well tissue culture microtiter plates in culture medium F12/DMEM supplemented with insulin (10 µg/ml), transferrin (10 µg/ml), Selenium (10 nM), progesterone (3 nM), pokerweed mitogen (2.5 µg/ml), IL-2 (10 ng/ml) and heat inactivated fetal bovine serum (5%). The addition of fetal bovine serum is optional. This medium can support the clonal expansion of the B cells previously activated before selection. Plate the selected B cells in one 96 well plate for every $10^8$ starting lymphocytes. For the B cells selected from the lymphocyte-pool without pre-selection activation with antigens, feeder cells either UV irradiated lymphocytes ($10^6$ cells/well) or human liver stromal cells ($10^4$ cells/well) were added. Both feeder cells supported the proliferation of B cells. The cells were cultured at 37° C. and 5% $CO_2$. The culture medium was half changed in three days. At the end of the culture, usually 6-10 days, the culture was either fixed for immunocytochemistry or used for total RNA extraction.

Example 5

Immunocytochemistry

Immunocytochemical analyses was conducted to confirm that the expanded non-transformed B cells maintain the ability to produce antibodies. The cultures in 96 well plates were centrifuged at 2500 rpm for 10 minutes. The medium was carefully removed and the cells were immediately fixed with ethanol (−20° C.) and air dry. The fixed cultures were then treated with 3% $H_2O_2$ in 100% ethanol at room temperature for 30 minutes to inactivate endogenous peroxidase activity and followed by three rinses with PBS to remove residual H$_2$O$_2$. The cultures were incubated with horse radish peroxidase conjugated anti-human kappa light chain antibody (Sigma, Cat# A7164) diluted at 1:100 in PBS with 10% fetal bovine serum and 0.1% tween 20. After 2 hours incubation at room temperature, the cultures were washed three times with PBS and twice with freshly prepared Milli-O® water. Finally the cultures were incubated for 5 minutes with peroxidase substrate diaminobenzadine (1 mg/ml) prepared in sodium acetate buffer, pH 5.05, and H$_2$O$_2$ (0.003%). At the end of incubation, the cultures were washed with water and examined under microscope. B cells expressing kappa light chain were stained red brown color. The number of wells containing kappa-light-chain-positive colonies as well as the number of positive cells in each well was counted. The results showed the proportion wells containing kappa-light-chain-positive colonies varied largely from one preparation to the other, from 0 up to 95%. The variation depended on individual donor of lymphocytes and was therefore expected. The average size of colonies was about 20 cells. The largest colonies had about a hundred cells Example 6

Isolation of Immunoglobulin Genes

Total RNA was extracted from individual well of cultures with Qiagen Mini-spin total RNA isolation kit. The final elution volume was 30 µl. The first strand cDNA was synthesized with first strand cDNA synthesis kit using either a light chain reverse transcription primer (ctc tcc cct gtt ga) (SEQ ID NO: 1) or a heavy chain reverse transcription primer (agt ttt gtc aca aga) (SEQ ID NO: 2) (1 µM) in a 10 µl reaction mixture of 4.6 µl total RNA sample, 20 mM Tris, pH 8.3, 100 mM KCl, 5 mM MgCl$_2$, 1 mM each of the deoxynucleotides (dATP, dTTP, dCTP and dGTP), 25 units of RNAase inhibitor, and 10 units of AMV reverse transcriptase. The reaction was carried out with a thermacycler set at 37° C. for 10 minutes, 42° C. for 60 minutes and 99° C. for 10 minutes.

The second strand of light chain cDNA was synthesized with a degenerated primer (gga gaa ata gtg atg ac (c/t/g) cag (t/a)ct c) (SEQ ID NO: 3), 1 unit Taq polymerase, and 1 unit Klenow fragment of DNA polymerase. The reaction was carried out at 37° C. for 10 minutes, then the temperature was raised to 50° C. at a rate of 2° C. per minutes, and finally to a temperature of 72° C. for 1 minute. Amplification of the light chain was completed by polymerase chain reaction with addition of an amplification primer (tca ctc tcc cct gtt gaa get ctt) (SEQ ID NO: 4) and dilution of the reaction mixture to 50 µl of 10 mM Tris, pH 8.3, 50 mM KCl, and 1.5 mM MgCl$_2$. The PCR was run 45 cycles of 95° C. for 30 seconds, 63° C. for 60 seconds and 72° C. for 20 seconds. At the end of the cycles, the final extension was allowed at 72° C. for 7 minutes. The PCR products were fractionated on 1% agarose gel in Tris-Borate EDTA buffer for 5 hours at 75 volts. The predicted size of light chain product was about 630 bp.

The synthesis and amplification of heavy chain was similar to the light chain. During second chain synthesis, a primer (ct cag tgt cag atc ctc a(c/t)c atg g) (SEQ ID NO: 5) was annealed to the site of start codon of heavy chains. For PCR, an amplification primer (tca agt ttt gtc aca aga ttt ggg ctc aa) (SEQ ID NO: 6) was used. The setting for thermacycler was the same as light chains.

Example 7

Cloning of the PCR Product

The amplified DNA products were subjected to gel electrophoresis. The cDNA band of predicted size was excised and purified with Qiagen gel purification kit. Heavy chain cDNA was immediately ligated to a pTargeT vector at 4° C. overnight with a TA cloning kit purchased from Promega. For light chains, a signal peptide cDNA (primer used: atg gaa acc cca gct cag ctt ctc ttc ctc cta cta ctc tgg ctc cca gat acc act gga gaa ata gtg atg ac (SEQ ID NO: 7) and tca gtt gaa gct ctt tgt gac (SEQ ID NO: 8)) was attached to their 5'-prime by a second round PCR and the product was purified again with the gel purification kit. The final product was ligated to pTargeT vector. The ligated products were transformed into J109 strain of E Coli and plated on LB/ampilcilin/x-Gal/IPTG plates. The plates were cultured at 37° C. overnight. Each plate normally results in hundreds of white colonies.

Example 8

Expression of the Immunoglobulin cDNA in Mammalian Cells

The pTargeT™ vector contain a CMV promotor which allow the cDNA inserts to be expressed in mammalian cells, a T7 promotor which allow prokaryote expression, and a neo gene coding for G418 resistance. To confirm that the immunoglobulin mRNA from clonal B cells has been successfully amplified and cloned into pTargeT™ plasmid, we made a mini-prep of the plasmid DNA from a pool of about 200 white colonies grown on each of the above LB plate. We then transfect the plasmid DNA into COS cells with lipofectamine reagents from Gibco BRL. Briefly, 1 µg of plasmid DNA was diluted in 100 µl F12 DMEM and 5 µl of Lipofectamine® reagent was diluted in 100 µl F12/DMED. To make tranfection mixture, the two solutions were immediately mixed together and stood at room temperature for 15 minutes. The mixture was then diluted with 800 µl F12/DMEM and layered onto COS cell monolayer which had been of 50% confluence and washed with serum free medium. The COS cells were incubated with the tansfection mixture for 4 hours at 37° C. Then the transfection mixture was removed and the cells were washed once with serum free medium and fed with F12/DMEM with 10% serum. After 24 hours, the cultures were washed with PBS, fixed with ethanol and processed for immunocytochemistry.

Upon identification of immunoglobulin-expressing COS cells, the pool of plasmids was then re-transformed into cells to isolate specific colonies. PCR, prokaryotic expression, and mammalian expression with antibody detection were used to screen the specific colonies. When both light chain and heavy chain had been cloned from individual B cell clones, the light chain and heavy chain were co-expressed in mammalian cell to produce human monoclonal antibodies either directly as Fab or as whole immunoglobulin after subcloning into a vector containing Fc fragments. Stable cell line could be established for continuous production of human antibodies.

I claim:

1. An isolated population of non-transformed human B cell clones that produce human monoclonal antibodies immunoreactive with cell surface antigens, wherein said isolated population of non-transformed human B cell clones is generated by:
    (a) (1) culturing in vitro in an immunization medium, an isolated population of human lymphocytes comprising a plurality of non-transformed human B lymphocytes and cells that natively express said cell surface antigens that have been immobilized to a solid substrate, and thereby contacting said isolated population of human lymphocytes comprising said plurality of non-transformed human B lymphocytes with said cells that natively express said cell surface antigens that have been immobilized to the solid substrate, and (2) allowing one or more non-transformed human B lymphocytes to specifically bind to the immobilized cells bearing said cell surface antigens, wherein the surfaces of the non-transformed human B lymphocytes are free of serum, and (b) removing unbound B lymphocytes thereby selecting the non-transformed human B lymphocytes that specifically bind to the cells bearing the cell surface antigens, and (c) culturing the selected B lymphocytes of (b) under conditions favorable for B cell proliferation to yield a plurality of non-transformed B cell clones that produce human monoclonal antibodies immunoreactive with the cell surface antigens.

2. The isolated population of non-transformed human B cell clones of claim 1, said human B cell clones produce a population of human monoclonal antibodies exhibiting binding specificity to the cell surface antigens representative of the specific cell type.

3. The isolated population of non-transformed human B cell clones of claim 1, wherein the cells that natively express said cell surface antigens have been grown in serum-free medium.

4. The isolated population of non-transformed human B cell clones of claim 1, wherein the cells that natively express said cell surface antigens are grown in the form of a monolayer.

5. The isolated population of non-transformed human B cell clones of claim 1, wherein the cells that natively express said cell surface antigens are of embryonic or adult origin.

6. The isolated population of non-transformed human B cell clones of claim 1, wherein the cells that natively express said cell surface antigens are human cells.

7. The isolated population of non-transformed human B cell clones of claim 1, wherein the cells that natively express said cell surface antigens are eukaryotic cells.

8. The isolated population of non-transformed human B cell clones of claim 1, wherein the cell surface antigens are presented on the surface of an intact cell.

* * * * *